United States Patent [19]

Tachikawa

[11] Patent Number: 5,281,736
[45] Date of Patent: Jan. 25, 1994

[54] METHOD FOR THE PREPARATION OF 1-AZA-2-SILACYCLOPENTANE COMPOUNDS

[75] Inventor: Mamoru Tachikawa, Kanagawa, Japan

[73] Assignee: Dow Corning Japan, Ltd., Tokyo, Japan

[21] Appl. No.: 81,754

[22] Filed: Jun. 23, 1993

[30] Foreign Application Priority Data

Jul. 6, 1992 [JP] Japan .................. 4-178643

[51] Int. Cl.$^5$ .................................................. C07F 7/10
[52] U.S. Cl. .................................................. 556/407
[58] Field of Search ........................................ 556/407

[56] References Cited

U.S. PATENT DOCUMENTS

5,136,064  8/1992  King et al. ...................... 556/407

OTHER PUBLICATIONS

J. L. Speier, C. A. Roth, J. W. Ryan, J. Org. Chem, vol. 36, No. 21, 3121 (1971).
M. G. Voronkov, S. V. Kirpichenko, A. T. Abrosimova, A. I. Albanov J. Organomet. Chem., 406, 87-89 (1991).

*Primary Examiner*—Paul F. Shaver
*Attorney, Agent, or Firm*—William F. Boley

[57] ABSTRACT

The present invention relates to a method for the preparation of 1-aza-2-silacyclopentane compounds whose nitrogen is substituted by a hydrocarbon group or a heteroatom-containing hydrocarbon group. The method comprises effecting an intramolecular hydrosilylation reaction of a N,N-disubstituted aminosilane. In a preferred method, the intramolecular hydrosilylation reaction is conducted in the presence of a rhodium-containing catalyst.

7 Claims, No Drawings

METHOD FOR THE PREPARATION OF 1-AZA-2-SILACYCLOPENTANE COMPOUNDS

BACKGROUND OF INVENTION

The present invention relates to a method for the preparation of 1-aza-2-silacyclopentane compounds whose nitrogen is substituted by a hydrocarbon group or a heteroatom-containing hydrocarbon group. The method comprises effecting an intramolecular hydrosilylation reaction of a N,N-disubstituted aminosilane. In a preferred method the intramolecular hydrosilylation reaction is conducted in the presence of a rhodium-containing catalyst.

Among the 1-aza-2-silacyclopentane compounds known to date, 1-aza-2-silacyclopentane compounds having a carbon atom bonded at the 1 position (nitrogen atom) include 1,2,2-trimethyl -1-aza-2-silacyclopentane, 1-benzyl-2,2-dimethyl-1-aza -2-silacyclopentane, 1-phenyl-2,2-dimethyl-1-aza-2-silacyclopentane, 1,2,2,4-tetramethyl-1-aza-2-silacyclopentane, 1-(beta-aminoethyl)-2,2,3-trimethyl-1-aza-2-silacyclopentane, and so forth. The synthesis reactions of these compounds generally involve combinations of some number of equivalent reactions and are disadvantageous from an industrial perspective because of the problem of dealing with by-products as well as the number of steps in the production process.

For example, one method consists of the reaction of a (3-chloroalkyl)chlorosilane (e.g., $ClCH_2CH_2CH_2SiR_2CL$) ) with an excess of primary amine (J. L. Speier, C. A. Roth, J. W. Ryan, J. Org. Chem., Vol. 36, No. 21, 3121 (1971)). The drawbacks to this reaction are as follows: the starting (3-chloroalkyl)silanes are difficult to obtain in high yields, and the reaction produces 2 equivalents of ammonium salt as a by-product. Another method comprises the reaction of (3-chloroalkyl)hydrosilanes (e.g., $ClCH_2CH_2CH_2SiR_2H$) with an excess of primary amine (M. G. Voronkov, S. V. Kirpichenko, A. T. Abrosimova, A. I. Albanov, J. Organomet. Chem., 406, 87-9 (1991)). The problems with this reaction are that the starting (3-chloroalkyl)hydrosilanes are difficult to obtain and the reaction produces ammonium salt as a by-product.

The present invention makes possible the selective, high-yield preparation of 1-aza-2-silacyclopentane derivatives that have nonhydrolyzing functional groups on the N atom from the silyl derivatives of secondary allylamines, without generating ammonium salts as by-products.

The 1-aza-2-silacyclopentane derivatives of the present invention are useful as aminoalkyl-containing silane coupling agents that carry a hydrocarbyl group (e.g., allyl, phenyl, substituted phenyl, benzyl, substituted benzyl, and so forth) on the nitrogen atom, and are also useful as the corresponding end-stopping agents for polysiloxanes. Moreover, because of the high reactivity of the nitrogen-silicon bond, these derivatives can be used to synthesize a large number of organofunctional silane derivatives by ring-opening reactions and insertion reactions.

SUMMARY OF INVENTION

The present invention relates to a method for the preparation of 1-aza-2-silacyclopentane compounds whose nitrogen is substituted by a hydrocarbon group or a heteroatom-containing hydrocarbon group. The method comprises effecting an intramolecular hydrosilylation reaction of a N,N-disubstituted aminosilane. In a preferred method, the intramolecular hydrosilylation reaction is conducted in the presence of a rhodium-containing catalyst.

DESCRIPTION OF INVENTION

The present invention takes as its object the introduction of a process for the selective, high-yield preparation of compounds described by formula (II) below, which does not produce ammonium salt by-product and which starts from aminosilanes that can themselves be synthesized from halohydrosilanes and secondary amines that are easily acquired or manufactured industrially.

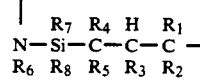

(II)

In formula (II), $R^1$, $R^2$, $R^3$, $R^4$, and $R^5$ are independently selected from a group consisting of hydrogen atom and hydrocarbon groups, each $R^7$ and $R^8$ is independently selected from a group consisting of hydrocarbon groups, and $R^6$ is an organic group selected from a group consisting of (i) saturated or unsaturated monovalent hydrocarbon groups comprising 1 to 14 carbon atoms and (ii) groups represented by $-R^9-A$ in which $R^9$ is a saturated or unsaturated divalent hydrocarbon group comprising 1 to 13 carbon atoms and A is a saturated or unsaturated monovalent organic group comprising 1 to 13 carbon atoms that contains at least one atom chosen from a group consisting of nitrogen, oxygen, sulfur, silicon, fluorine, chlorine, bromine, and iodine, with the proviso that the sum of the number of carbon atoms in $R^9$ and the number of carbon atoms in A does not exceed 14.

The present invention comprises a method for the preparation of 1-aza-2-silacyclopentane compounds with general formula (II), as previously described, in which N,N-disubstituted aminosilane described by formula (I)

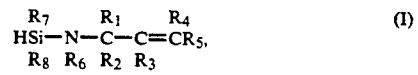

(I)

where $R^1$, $R^2$, $R^3$, $R^4$, $R^5$, $R^6$, $R^7$, and $R^8$ are defined as above, is subjected to an intramolecular hydrosilylation reaction.

The aforementioned hydrosilylation reaction is preferably carried out using a rhodium-containing catalyst. This rhodium-containing catalyst can be metallic rhodium, carrier-supported rhodium metal, colloidal rhodium metal, a zero-valent rhodium complex, a monovalent rhodium complex, or a trivalent rhodium complex. Among these, monovalent rhodium complexes, for example, tris(triphenylphosphine)rhodium(I) chloride, 1,5-cyclooctadienerhodium(I) chloride dimer, and so forth, and trivalent rhodium compounds such as, for example, rhodium trichloride trihydrate, are particularly desirable.

In the present invention, the hydrocarbon groups represented by $R^1$, $R^2$, $R^3$, $R^4$, and $R^5$ are preferably saturated or unsaturated hydrocarbon groups that contain 1 to 7 carbon atoms, for example, alkyl groups such as methyl, ethyl, propyl, isopropyl, and butyl; aralkyl groups such as benzyl; and aryl groups such as phenyl and tolyl.

From the standpoint of the reactivity of the azasilacyclopentane product and ease of acquisition of the starting secondary amine, it is particularly preferable that $R^1$, $R^2$, and $R^3$ be hydrogen or methyl and that $R^4$ and $R^5$ be hydrogen or hydrocarbon groups have relatively few carbons, such as methyl, ethyl, or isopropyl. $R^7$ and $R^8$ are preferably identical or different hydrocarbon groups comprising 1 to 6 carbon atoms, and can be exemplified by methyl, ethyl, isopropyl, propyl, phenyl, and so forth. $R^6$ is an alkyl group such as ethyl, propyl, isopropyl, butyl, and hexyl; an alkenyl group such as vinyl, allyl, and propenyl; an aralkyl group such as benzyl; an aryl group such as phenyl, and tolyl; a 2-aminoethyl group; or a substituent that itself contains the azasilacyclopentane structure, as represented in formulas (III) and (IV) below.

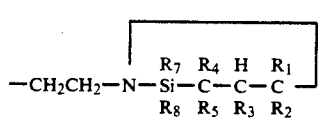

(III)

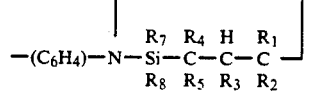

(IV)

Azasilacyclopentanes that can be produced in accordance with the present invention are nonexhaustively exemplified by 1-allyl-2,2-dimethyl-1-aza-2-silacyclopentane, 1-phenyl-2,2-dimethyl-1-aza-2-silacyclopentane, 1-benzyl-2,2-dimethyl-1aza-2-silacyclopentane, 1-vinylbenzyl-2,2-dimethyl-1-aza-2-silacyclopentane, and the following formulas (V) and (VI).

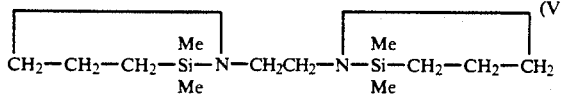

(V)

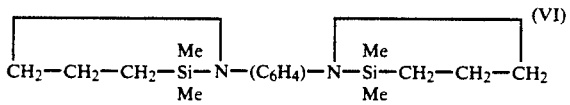

(VI)

The compounds represented by formula (II) may be employed either directly or as separate compounds produced by their reaction with other compounds for the modification of silicone compounds, other organic compounds, and organic polymers.

The present invention is explained in greater detail in the following examples, but the invention is not limited to these examples. Also, in the following examples, unless expressly indicated otherwise, "part" means "weight part" and "%" means "mol%". For the examples provided, the products were isolated and purified by distillation or preparative gas chromatography, and their structures were confirmed by $^1$H-NMR, $^{13}$C-NMR, $^{29}$Si-NMR, and mass spectrometric analysis, as appropriate.

Reference Example 1. (Preparation of N-dimethylsilyldiallylamine) Into a nitrogen-flushed vessel were introduced 21 parts diallylamine, 29 parts triethylamine, and 200 parts heptane, and, while agitating, a mixture of 50 parts heptane and 22 parts dimethylchlorosilane was slowly dripped in. After 2 days, another 200 parts heptane was added, and the mixture was filtered to remove the precipitate. The filtrate was distilled to obtain N-dimethylsilyldiallylamine in a yield of 84% based on diallylamine.

Reference Example 2. (Preparation of N-dimethylsilyl -N-allylaniline) Into a nitrogen-flushed container were introduced 25 parts N-allylaniline, 28 parts triethylamine, and 200 parts hexane, and, while agitating, a mixture of 25 parts dimethylchlorosilane was slowly dripped in. The resulting slurry was heated at reflux for 18 hours, cooled to room temperature, and filtered to remove the precipitate. The filtrate was distilled to obtain N-dimethylsilyl-N-allylaniline in a yield of 64% based on N-allylaniline.

Reference Example 3. (Preparation of N-dimethylsilyl-N-benzylallylamine) Into a nitrogen-flushed container were introduced 18 parts N-benzylaniline and 50 parts ethyl ether, and while cooling in a water bath 74 parts n-butyllithium/hexane (1.6 mol/L) was slowly dripped in. Then, 11.5 parts dimethylchlorosilane was slowly dripped in. The resulting precipitate was filtered, and the filtrate was distilled to give N-dimethylsilyl-N-benzylallylamine in a yield of 85% based on N-benzylaniline.

Example 1. Into a nitrogen-flushed vessel were introduced 1 part N-dimethylsilyldiallylamine, 3 parts benzene, and 0.003 part tris(triphenylphosphine)chlororhodium ($RhCl(PPh_3)_3$). The mixture was heated at reflux for 4 hours in an oil bath. No N-dimethylsilyldiallylamine was observed. 1-Allyl-2,2-dimethyl-1-aza-2-silacyclopentane and 1propenyl-2,2-dimethyl-1-aza-2-silacyclopentane were produced in a molar ratio of 98:2 and a combined yield of 95%.

Example 2. Into a glass tube with an outside diameter of 10 mm and a length of 10 cm were introduced 2 mg $RhCl(PPh_3)_3$ and 2 mL of a mixture of 1 part N-dimethylsilyldiallylamine and 3 parts benzene, and the tube was sealed. After heating this for 17 hours at 80° C., the conversion was 100 weight % and 1-propenyl -2,2-dimethyl-1-aza-2-silacyclopentane was obtained in a yield of 98%. No production of 1-allyl-2,2,3-trimethyl-1-aza-2-silacyclobutane was observed.

Example 3. Into a glass tube with an outside diameter of 10 mm and a length of 10 cm were introduced 5 mg $((1,5-cyclooctadiene)RhCl)_2$ and 2 mL of a mixture of 1 part N-dimethylsilyl-N-benzylallylamine and 2 parts toluene, and the tube was sealed. After this had been left quiescent for 30 minutes at room temperature, the conversion of N-dimethylsilyl-N-benzylallylamine was 100 weight %. 1-Benzyl-2,2-dimethyl-1-aza-2-silacyclopentane was obtained in a yield of 96%. No production of 1-benzyl-2,2,3-trimethyl-1-aza-2-silacyclobutane was observed.

Example 4. A sealed glass tube reaction was carried out as in Example 2, except for employing 2 mg tris(triphenylphosphine)chlororhodium($RhCl(PPh_3)_3$) as catalyst and 2 mL of a mixture of N-dimethylsilyl-N-benzylallylamine and benzene (molar ratio 38:62) and reacting for 9 hours at 80° C. The conversion of starting material was 100 weight %, and the yield of 1-benzyl-2,2-dimethyl-1-aza-2-silacyclopentane was 98%. No isomeric azasilacyclobutane was produced.

Example 5. A sealed glass tube reaction was carried out as in Example 2, except for employing 2 mg tris(triphenylphosphine)chlororhodium ($RhCl(PPh_3)_3$) and 2 mL of a mixture of N-dimethylsilyl-N-allylaniline and benzene (molar ratio 40:60) and reacting for 15 hours at 60° C. The conversion of starting material was 100 weight %. The yield of 1-phenyl -2,2,3-trimethyl-1-aza-2-silacyclobutane was 4%, and that of 1-phenyl-2,2-dimethyl-1-aza-2-siacyclopentane was 72%.

Example 6. A sealed glass tube reaction was carried out as in Example 2, but in this case employing 1 mL N -dimethylsilyl-N-benzylallylamine and 1 mg rhodium trichloride trihydrate and heating for 5 minutes at 120° C. The conversion of the starting material was 100 weight %, and the yield of 1-benzyl -2,2-dimethyl-1-aza-2-silacyclopentane was 97 %. No isomeric azasilacyclobutane was produced.

Comparison Example 1. Into a nitrogen-flushed container were introduced 1 part N-dimethylsilyldiallylamine, 3 parts benzene, and 0.003 part bis(triphenylphosphine)dichloro-platinum (PtCl$_2$(PPh$_3$)$_2$), and the mixture was heated at reflux in an oil bath for 4 hours. No N-dimethylsilyldiallylamine was observed. 1-Allyl-2,2,3-trimethyl-1-aza-2-silacyclobutane and 1-allyl-2,2-dimethyl-1-aza-2-silacyclopentane were produced in a molar ratio of 83:17 and a combined yield of 77%. A mixture of these two products was obtained at a yield of 70% by reduced pressure distillation.

Comparison Example 2. Into a glass tube with an outside diameter of 10 mm and a length of 10 cm were introduced 0.002 mL of a 20 weight % isopropanolic chloroplatinic acid solution and 2 mL of a mixture of 1 part N-dimethylsilyldiallylamine and 3 parts benzene, and the tube was sealed. The tube was heated for 17 hours at 80° C. The conversion of starting material was 100 weight %. 1-Allyl-2,2,3-trimethyl-1-aza-2-silacyclobutane and 1-allyl-2,2-dimethyl-1-aza -2-silacyclopentane were produced in a molar ratio of 66:34 and a combined yield of 55%.

Comparison Example 3. A sealed glass tube reaction was carried out as in Comparison Example 2, but in the present case using 10 mg platinum on activated carbon (5 weight % Pt/C) and 2 mL of a mixture of N-dimethylsilyl-N-benzylallylamine and benzene (molar ratio 38:62) and reacting the mixture for 15 hours at 60° C. The conversion of the starting material was 100 weight %. The yield of 1-benzyl-2,2,3-trimethyl-1-aza-2-silacyclobutane was 84% and that of 1-benzyl-2,2-dimethyl-1-aza-2-silacyclopentane was 16%.

Comparison Example 4. A sealed glass tube reaction was carried out as in Comparison Example 2, but in this case using 2 mg bis(triphenylphosphine)dichloro-platinum (PtCl$_2$(PPh$_3$)$_2$) and 2 mL of a mixture of N-dimethylsilyl-N-benzylallylamine and benzene (molar ratio 38:62) and reacting for 15 hours at 60° C. The conversion of starting material was 95 weight %. The yield of 1-benzyl-2,2,3-trimethyl-1-aza-2-silacyclobutane was 92 % and that of 1-benzyl-2,2-dimethyl-1-aza-2-silacyclopentane was 2%.

We claim:

1. A method for preparation of 1-aza-2-silacyclopentane compounds described by formula

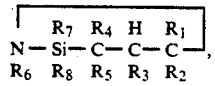

the method comprising: effecting an intramolecular hydrosilylation reaction of a N,N-disubstituted aminosilane described by formula

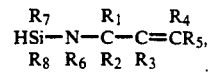

where each $R^1$, $R^2$, $R^3$, $R^4$, and $R^5$ is independently selected from a group consisting of hydrogen atom and hydrocarbon groups, each $R^7$ and $R^8$ is independently selected from a group consisting of hydrocarbon groups, and $R^6$ is an organic group selected from a group consisting of (i) saturated or unsaturated monovalent hydrocarbon groups comprising 1 to 14 carbon atoms (ii) and groups represented by -$R^9$-A in which $R^9$ is a saturated or unsaturated divalent hydrocarbon group comprising 1 to 13 carbon atoms and A is a saturated or unsaturated monovalent organic group comprising 1 to 13 carbon atoms that contains at least one atom chosen from a group consisting of nitrogen, oxygen, sulfur, silicon, fluorine, chlorine, bromine, and iodine, with the proviso that the sum of the number of carbon atoms in $R^9$ and the number of carbon atoms in A does not exceed 14.

2. A method according to claim 1 where, the intramolecular hydrosilylation reaction is effected using a rhodium-containing catalyst.

3. A method according to claim 2, where the rhodium-containing catalyst is selected from a group consisting of a monovalent rhodium complex and a trivalent rhodium complex.

4. A method according to claim 2, where the rhodium-containing catalyst is selected from a group consisting of tris(triphenylphosphinerhodium(I) chloride, 1,5-cyclooctadienerhodium(I) chloride dimer, and rhodium trichloride trihydrate.

5. A method according to claim 1, where $R^1$, $R^2$, $R^3$, $R^4$, and $R^5$ are independently selected from a group consisting of hydrogen atom and saturated and unsaturated hydrocarbon groups comprising one 1 to 7 carbon atoms and $R^7$ and $R^8$ are selected from a group consisting of hydrocarbon groups comprising 1 to 6 carbon atoms.

6. A method according to claim 5, where $R^6$ is selected from a group consisting of ethyl, propyl, isopropyl, butyl, hexyl, vinyl, allyl, propenyl, benzyl, phenyl, and tolyl.

7. A method according to claim 5, where $R^6$ is selected from a group consisting of

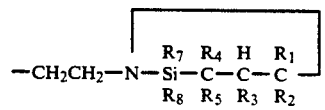

and

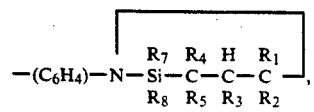

where $R^1$, $R^2$, $R^3$, $R^4$, $R^5$, $R^7$, and $R^8$ are as previously described.

* * * * *